United States Patent [19]

Page et al.

[11] Patent Number: 5,200,330
[45] Date of Patent: Apr. 6, 1993

[54] METHOD FOR THE PREPARATION OF METHYL ANTHRANILATE

[75] Inventors: Gregory V. Page, Maplewood; Bonita Scire, East Brunswick; Mohamed I. Farbood, Holmdel, all of N.J.

[73] Assignee: BASF K&F Corporation, Parsippany, N.J.

[21] Appl. No.: 582,829

[22] Filed: Sep. 14, 1990

Related U.S. Application Data

[62] Division of Ser. No. 70,062, Jul. 6, 1987, abandoned.

[51] Int. Cl.$^5$ .................. C12P 13/00; C12P 13/02; C12P 7/62
[52] U.S. Cl. ..................... 435/128; 435/119; 435/135; 435/911
[58] Field of Search ............. 435/128, 135, 129, 911, 435/822, 830, 886, 921, 191

[56] References Cited

U.S. PATENT DOCUMENTS

T3,520,778  7/1970  Bellet et al. ................ 435/119
3,923,602  12/1975  Argoudelis ................. 435/886

OTHER PUBLICATIONS

Morrison et al., 1980, *Organic Chemistry*, p. 1007, Allyn and Bacon.
Gibson et al., Third European Congress on Biotechnology, vol. 3, 1984, pp. III-377-III-382.
Bellet and Van Thuong, "La N-Demethyl Ajmaline", Annal. Pharm. Francaises, 28:245-49 (1970).
Funderburk, Jr. et al., "Metabolism of Trifluralin By Soil Microorganisms and Higher Plants" (Abs. Only), Proc. Southern Weed Conf., 20:389 (1967).
Kaczkowski, J., "Mikrobiologiczny Rozklad Alkaloidow Tropanowych (Microbiological Decomposition of Tropane Alkaloids)", Acta. Soc. Btn. Polon., 28:677-694 (1959).
Kuwahara et al., "Production of Extracellular NAD and NADP by a Lignin-Degrading Fungus, Phanerochaete Chrysosporium", J. of Ferment. Technol., 62:237-242 (1984).
Mitscher et al., "Microbiological Transformation of 6,14-Endo-Ethenotetrahydrothebaine Alkaloids", Experientia, 24:133-134 (1968).
Read and McQueen, "Investigation of White-Rot Fungi for the Conversion of Poplar into a Potential Feedstuff for Ruminants", Can. J. of Microbiol., 29:457-463 (1983).
Shimazono and Nord, "Transformations of Anisic Acid and Methylanisate by the Mold Polystictus Versicolor", Arch. of Biochem. Biophys., 87:140-143 (1960).
Smolikova and Tichy, "The Effect of Phosphorus and Nitrogen on Some Physiological Activities of the Fungi Fomes Marginatus and Trametes Gibbosa", Biologia 5:211-217 (1976).
Taylor, B. F., "Aerobic and Anaerobic Catabolism of Vanillic Acid and Some Other Methoxy-Aromatic Compounds by Pseudomonas sp. Strain PN-1", Appl. Environ. Micribiol., 46:1286-1292 (1983).
Voigt and Bornschein, "Zur Entmethylierung von N-Methylchanoclavin-(1) durch Claviceps purpurea Tul." Pharmazie, 22:258-260 (1967).

*Primary Examiner*—Irene Marx
*Attorney, Agent, or Firm*—Kenyon & Kenyon

[57] ABSTRACT

A process for the preparation of "natural" methyl anthranilate which comprises the microbial N-demethylation of methyl N-methyl-anthranilate is disclosed.

8 Claims, No Drawings

METHOD FOR THE PREPARATION OF METHYL ANTHRANILATE

This application is a division of application Ser. No. 070,062, filed Jul. 6, 1987, abandoned.

BACKGROUND OF THE INVENTION

This invention is directed to a microbial method for preparation of methyl anthranilate from naturally occurring methyl N-methyl anthranilate.

In recent years there has been a considerable consumer preference for more and better "all natural" flavors. To meet this demand, there is a need to develop new methods for securing natural aroma chemicals.

Concord grape (*Vitis labrusca*) flavors represent a type of product which has enjoyed widespread use in the food industry. Methyl anthranilate is known to be the major contributor to the typical aroma of this fruit, and it is a valuable ingredient in many other flavoring systems. Although methyl anthranilate is widely distributed in nature, its isolation is not generally economical due to the extremely low levels present. Therefore an alternate method for obtaining natural methyl anthranilate is required.

Although methyl anthranilate is not easily obtained from natural sources, methyl N-methylanthranilate (hereinafter dimethyl anthranilate) is readily recovered from petitgrain mandarin leaf oil (*Citrus reticulata*) in a high yield. Consequently it would be desirable to take advantage of this ready availability to produce methyl anthranilate by a N-demethylation method.

Microbially mediated N-demethylation reactions have been reported in species of Pseudomonas (Taylor, B. F., in *Appl. Environ. Microbiol*, 46:1286, 1983), Streptomyces (Yamano, et al, in *Ann. Rep. Takeda Res. Lab*, 21:88, 1963 also Bellet and van Thuong U.S. Pat. No. 3,520,778 in 1970), Arthrobacter (Kaczkowski, J., in *Acta Soc. Botan.Polon.*, 28:677, 1959) Cunninghamella, Xylaria (Mitscher et al., in *Experientia*, 24:133, 1968), Claviceps (Voigt and Bornschein, in *Pharmazie*, 22:258, 1967) and Aspergillus (Funderburk et al., in *Proc. Southern Weed Conf.*, 20:389, 1967). Various types of N-dealkylation reactions have been reported in the degradation of lignin by dry-rot fungi, including members of the genera Phanerochaete (Kuwahara et al, in *J. Ferment. Technol.*, 62:237, 1984), Polyporus, Ganoderma. Fomitoosis (Reade and McQueen, in *Can. J. Microbiol* 29:457, 1983), Polystictus (Shimazono and Nord, in *Arch. Biochem. Biophys.*, 87:140, 1960), Trametes and Fomes (Smolikova and Tichy, in *Biologia*. 5:211, 1976).

Despite these reports, however, the microbial demethylation of dimethyl anthranilate has not been reported because, for one reason, both the starting material and the product are highly toxic to most microorganisms. Moreover, the substrate stereochemistry causes difficulty because the microbiological demethylations are enzymatic and hence are highly selective. As a result, no reported microbiological reaction can be applied as a general method for demethylation of substituted amines.

Therefore, it is an object of the invention to develop a microbiologically mediated demethylation method which unexpectedly will produce reasonable yields of methyl anthranilate. Another object is the development of a microbiological method which is effective despite the toxicity of the starting material and product.

SUMMARY OF THE INVENTION

These and other objects are achieved by the invention which is directed to a method for the microbiological conversion of the substrate dimethyl anthranilate into methyl anthranilate. According to this method, the dimethyl anthranilate is converted by cultivating it with a fungal microorganism. The microorganism is cultured in a nutrient broth and the substrate is added to the culture medium after an appropriate incubation period. The amount of substrate used can be up to about 10 weight percent, preferably up to about 2.0 weight percent, more preferably up to about 0.5 relative to the total weight of the broth, culture and substrate. A substrate analog such as 2,5-dimethyl aniline or N,N-dimethyl aniline may be added to the culture medium prior to substrate addition in order to increase the yield of the method. Protein synthesis inhibitors may also be used. A preferred microorganism for use in the present method is a wood rotting fungus or a fungus capable of degrading cellulose or lignin.

DETAILED DESCRIPTION OF THE INVENTION

According to this invention, a method has been discovered under which methyl anthranilate and more specifically "natural" methyl anthranilate can be produced by the microbial transformation of dimethyl anthranilate. The "natural" dimethyl anthranilate used in this transformation may preferably be recovered from natural sources, as for example, from petitgrain mandarin leaf oil (*Citrus reticulata*) by standard techniques such as extraction or distillation. Although dimethyl anthranilate and methyl anthranilate are generally toxic to most microorganisms, certain kinds of fungi can tolerate useful concentrations of these compounds up to about 10 percent relative to the total culture medium weight. Highly desirable concentrations in this regard are those up to about 2 percent. The fungi also are capable of general N-demethylation of substituted amines. Microorganisms, which are suitable for these purposes and produce desirable yields of methyl anthranilate, include, but are not limited to, various strains of Streptomyces (e.g., *S. rosechromogenus, S. purpuracens, S. lavendulae, S. griseus, S. platensis*), strains of Aspergillus (e.g., *A. oryzae, A. niger*), *Candida lipolytica. Yarowia lipolytica*, species of Xylaria (e.g., *X. digitata, X. hypoxylon, X. magnoliae*), species of Arthrobacter (e.g., *A. flavencens, A. globiformis, A. mysorens, A. variabilis, A. simplex*), *Cunninghamella echinulata* (several strains), and *Claviceps purpurea* (several strains). Highly desirable yields of methyl anthranilate can be obtained with virtually all genera of wood-rotting fungi, more preferably with species of the genera Trametes, Polystictus and Polyporus and most preferably *Trametes cingulata* ATCC 26747 and Polyporus sps ATCC 10089.

According to an embodiment of the process of the invention, a culture suspension is prepared by inoculation of a suitable nutrient broth with the chosen microorganism. A suitable nutrient broth is one which contains carbon sources, nitrogen sources, trace minerals and any required growth factors such as vitamins. Suitable carbon sources are preferably lactose, cellobiose, mannitol, sorbitol, ethanol, glycerol, more preferably monosaccharides such as maltose, fructose, rhamnose, xylose and most preferably glucose or malt extract. Suitable nitrogen sources include nitrogen-containing organic substances preferably peptone, meat extract, corn steep liquor and most preferably yeast extract. Inorganic nitrogen-containing compounds are also suitable including nitrates, nitrites and ammonium salts. These nutrients may be supplemented by addition of vitamins (particulary, those of the B-group) and/or trace minerals (such as Fe, Cu, Mo, Mn, P, Ca, and the like) to the medium, however, the process can be performed in unsupplemented medium if a small amount of yeast extract is added.

The inoculation according to an embodiment of the invention is carried out by adding the chosen microorganism culture into a suitable nutrient broth and allowing the organism to incubate at a suitable temperature and pH for 1 to 14 days prior to the addition of the substrate (i.e., dimethyl anthranilate). The length of this incubation period varies with the organism used, but growth of the culture can be monitored by measuring the disappearance of the carbon source, changes in pH or by visual observations (i.e., the appearance of turbidity or fungal mycelia in the culture broth).

The cultivation of the microorganism and substrate can be carried out as a stationary culture, but often higher yields can be obtained when the microorganism is grown in submerged culture (i.e., shake flask culture or fermentor culture) under aerobic conditions. A suitable pH range is from about 3.0 to about 8.0, and preferably about 5.0 to about 8.0 and especially about 6.0 to about 7.0. The pH may be regulated by the addition of inorganic or organic acids or bases. The incubation temperature is suitably between about 18° C. and about 33° C. with a range of about 20° to about 30° C. being preferred and especially a range of about 22° C. to about 26° C.

The fermentation may be carried out using the cells of the microorganism isolated from the culture broth or by enzymes isolated from the cells by the usual enzyme extraction techniques. When using the isolated enzyme, the reaction may be conveniently carried out in aqueous solutions (e.g., physiological saline, buffer solutions, fresh nutrient medium etc.) or the isolated cells or enzyme extract may be immobilized onto a solid support and the desired products can be made in the absence of the living organism. The transformation may also be carried out by mutants of the microorganism. These mutants can be readily obtained by methods well known in the art (e.g., UV irradiation, exposure to mutagenic compounds etc.).

In general, the substrate can be added directly to the fermentation broth after the microorganism has matured. An emulsion of dimethyl anthranilate and Tween-80 (mono-oleate) can be prepared such that the final concentration of dimethyl anthranilate in the broth is up to about 10 percent, preferably up to about 2 percent, and more preferably up to about 0.5 percent while the concentration of Tween-80 is up to about 1 percent. This reaction mixture is allowed to incubate for an additional 1 to 14 days, preferably 3 to 10 days and especially 4 to 8 days (depending upon the organism used) or until no further production of methyl anthranilate is observed.

Under the usual conditions employed for the process of the invention, a minor amount of N-formyl-methyl anthranilate is also produced. The two products thus are typically present as a mixture in the broth when fermentation is completed. This mixture of N-formyl-methyl anthranilate and methyl anthranilate in combination with unreacted dimethyl anthranilate can be isolated and the 3 individual components separated by conventional techniques (e.g., solvent extraction, distillation and chromatographic separation techniques). N-formyl-methyl anthranilate is easily converted to methyl anthranilate by base or heat catalyzed decarbonylation, and, if desired, the yield of methyl anthranilate can be increased by utilizing this reaction. In all cases there was a recovery of 95 to 98% of the starting materials and products by weight (i.e., none of the microorganisms degraded the starting material to undesired by-products) and GLC purities of >95% were usually obtained after simple solvent extraction.

The following examples serve to illustrate embodiments of the invention. These examples are in no way meant to limit the scope of the claims which follow.

EXAMPLE I

*Trametes versicolor* Fermentation Using Yeast-Malt Culture

Five flasks containing 100 mL each of yeast-malt (YM) broth (Difco Laboratories) were autoclaved at 121° C. for 20 min. After cooling, each flask was inoculated with 5 mL of a 3-day old YM broth culture of *Trametes versicolor* ATCC 42394. Each culture was incubated at 30° C. and 200 rpm on a rotary incubator/shaker for 3 days. Various aliquots of an emulsion of Tween-80 and dimethyl anthranilate (DMA) were added to each culture in order to give final dimethyl anthranilate concentrations of 0.2, 0.5, 1.0, 5.0 and 10.0% in the fermentation broth. Each culture was incubated an additional 6 days and the results as percent concentration of methyl anthranilate (MA) are shown in Table I. (*Trametes versicolor* ATCC 42394 is also described in the ATCC Catalogue of Filamentous Fungi, 18th ed (1991) as *Polyporus versicolor* ATCC 42394).

TABLE I

Effect of Initial DMA Concentration on MA Yields with *Trametes versicolor* Strain 42394 Grown in YM Broth*

| Initial DMA Concentration (%) | 3 Days Incubation | MA Concentration (%) 6 Days Incubation |
|---|---|---|
| 10.0 | 0.3 | 1.5 |
| 5.0 | 2.6 | 4.0 |
| 1.0 | 8.7 | 11.9 |
| 0.5 | 18.7 | 26.5 |
| 0.2 | 28.7 | 32.8 |

*N-formyl-methyl anthranilate was also detected in the above but not quantitated. Later data indicated that 2% conversion to N-formyl-methyl anthranilate was obtained with an initial DMA concentration of 1%.

EXAMPLE II

Trametes Fermentation Using Mineral Salts Culture

Using procedures and materials similar to those described in Example I, but substituting a mineral salts solution containing NH$_4$NO$_3$ (3 g/L), K$_2$HPO$_4$ (1.3 g/L), MgSO$_4$.7 H$_2$O. (0.5 g/L), KCl (0.5 g/L), FeSO$_4$ (0.01 g/L), yeast extract (5 g/L) and glucose (15 g/L) instead of, YM broth, to cultivate the microorganism, results were obtained which were similar in MA concentration and incubation period to the results presented in foregoing Table I.

EXAMPLE III

Other Trametes Fermentation

Using the procedures and materials described in Example I but substituting other members of the genus Trametes. including, *T. versicolor* strains ATCC 34578, 42394, 32085, 11235, 32745, 12679, 34584, 38068, 38070, 42462, 44677, *T. carbonaria* 26746, *T. cingulata* 26747, *T. cubensis* 14590, *T. extenuatus* 26174, *T. gibbosa* 34670, or *T. hispida* 36206 or substituting members of the genera Streptomyces, Candida, Xylaria, Arthobacter, Cunninghamella and Claviceps, results like those described in Example I were obtained.

EXAMPLE IV

Polyporus sp. Fermentation

Using procedures and materials similar to those described above for Example I but substituting Polyporus sp. ATCC 10089 as the microorganism results similar to those of Example I were obtained (Polyporus sp. ATCC 10089 is also described in the ATCC Catalogue of Filamentous Fungi, 18th ed (1191) as *Polyporus zonalis* ATCC 10089). By using a 7-day old culture of this organism (grown in double strength YM broth) to which was added 2% dimethyl anthranilate and 1% Tween-80, and allowing the reaction to continue for an additional 7 days 19.7% conversion to methyl anthranilate and 9.8% conversion to N-formyl-methyl anthranilate was measured.

EXAMPLE V

Extended Polyporus sp. Fermentation

Using procedures and materials similar to those described above for Example I but extending the incubation period of Polyporus sp. 10089 to 13 days prior to the addition of 2% dimethyl anthranilate, followed by an additional 11 days of incubation, 34.8% of the starting material is converted to methyl anthranilate (which represents 7 g methyl anthranilate/liter of broth) and 14.2% is converted to N-formyl-methyl anthranilate (or 2.8 g/L), with the remainder being recovered as dimethyl anthranilate.

EXAMPLE VI

A typical natural concord grape flavoring in a propylene glycol carrier, suitable for use in a still or carbonated beverage at a use level of approximately 0.5–1.0% was prepared as follows:

| Ingredient | Percent |
|---|---|
| Methyl Anthranilate | 0.10 |
| Ethyl Acetate | 1.00 |
| Ethyl Butyrate | 0.30 |
| Ethyl Isovalerate | 0.15 |
| Ethyl Propionate | 0.30 |
| Oil Orange FCC Florida | 0.01 |
| Acetic Acid | 1.50 |
| Propylene Glycol | 20.0 |
| Water, deionized | 36.34 |
| Concord Grape Juice Conc. 68 = Brix | 40.00 |
| | 100.00 |

The ingredients except the water and juice concentrate were mixed together, water and concentrate blended and the mixture stirred until a clear solution was obtained. Carbonation under pressure produced the desired grape drink.

EXAMPLE VII

A typical natural flavor, (concord grape type) system in a vegetable oil carrier, suitable for use in chewing gum at a use level of approximately 0.5–1.0% was prepared as follows:

| Ingredient | Percent |
|---|---|
| Ethyl Butyrate Natural | 2.0 |
| Ethyl Propionate Natural | 8.0 |
| Glacial Acetic Acid | 4.5 |
| Methyl Anthranilate Natural | 5.0 |
| Dimethyl Anthranilate Natural | 5.0 |
| Ethyl Acetate Natural | 4.0 |
| Vegetable Oil | 71.5 |
| | 100.0 |

The flavor can be combined with sugar and gumarabic base and extruded or shaped to provide chewing gum.

EXAMPLE VIII

A typical concord grape WONF flavoring in a grain alcohol carrier suitable for use in a still or carbonated beverage at a use level of approximately 0.5–1.0% was prepared as follows:

| Ingredient | Percent |
|---|---|
| Methyl Anthranilate Natural | 0.05 |
| Dimethyl Anthranilate Natural | 0.05 |
| Ethyl Acetate Natural | 1.00 |
| Ethyl Butyrate Natural | 0.30 |
| Ethyl Isovalerate Natural | 0.15 |
| Ethyl Propionate Natural | 0.30 |
| Oil Orange FCC Florida | 0.01 |
| Vinegar 120 grain | 4.00 |
| Grain alcohol | 20.00 |
| Water deionized | 34.14 |
| Concord Grape juice Conc. 68 = Brix | 40.00 |
| | 100.00 |

The ingredients except alcohol, water and juice concentrate, were mixed, the remaining ingredients blended in to form a single strength liquid and the liquid optionally carbonated to form the desired beverage.

A publicly available deposit of *Trametes (Polyporus) versicolor* ATCC 42394 is maintained by the American Type Culture Collection, Rockville, Md., pursuant to an agreement with the inventors herein, dated Sep. 28, 1992, pursuant to 37 CFR § 1.806.

We claim:

1. A method for the production of methyl anthranilate comprising:
    providing a microorganism selected from the group consisting of *Trametes versicolor* ATCC 42394 and Polyporus sp. ATCC 10089;
    incubating said microorganism under aerobic conditions with substrate methyl N-methyl anthranilate in a nutrient broth for a period of time at a pH and at a temperature effective to allow said microorganism to convert said substrate to methyl anthranilate, wherein said pH is in a range of from about 3 to about 9, said temperature is in a range of from about 18° C. to about 33° C. and said incubation period is from 1 to 14 days; and
    recovering the methyl anthranilate.

2. A method according to claim 1 wherein the methyl anthranilate is produced in mixture with methyl N-formyl anthranilate.

3. A method according to claim 2 further comprising converting the methyl-N-formyl anthranilate to methyl anthranilate by a base catalyzed or thermal decarbonylation reaction.

4. A method according to claim 1 wherein the pH is about 5 to about 8, the temperature is about 20° C. to about 30° C. and the incubation period is about 3 to 10 days.

5. A method according to claim 1 wherein the pH is about 6 to about 7, the temperature is about 22° C. to about 26° C. and the incubation period is about 4 to about 8 days.

6. A method according to claim 1 wherein the nutrient broth contains sources of organic nitrogen, carbohydrates, minerals and vitamins.

7. A method according to claim 1 wherein the methyl N-methyl anthranilate concentration is no more than about 2.0 percent.

8. A method according to claim 1 wherein the methyl N-methyl anthranilate concentration is no more than about 0.5 percent.

* * * * *